United States Patent [19]

Aikawa et al.

[11] Patent Number: 5,387,600
[45] Date of Patent: Feb. 7, 1995

[54] TREATING ARTERIOSCLEROSIS USING BENZIMIDAZOLE COMPOSITIONS

[75] Inventors: Kazuhiro Aikawa; Kozo Aoki, both of Minami-ashigara, Japan

[73] Assignee: Fuji Photo Film Co., Ltd., Kanagawa, Japan

[21] Appl. No.: 94,321

[22] Filed: Jul. 21, 1993

[30] Foreign Application Priority Data

Jul. 30, 1992 [JP] Japan .................. 4-204122
Sep. 2, 1992 [JP] Japan .................. 4-234767

[51] Int. Cl.⁶ .................. A61K 31/415; A61K 31/535
[52] U.S. Cl. .................. 514/395; 514/235.8; 514/237.5; 514/237.8; 514/387; 514/394; 514/392; 514/398; 514/400; 514/396
[58] Field of Search .............. 514/387, 395, 384, 392, 514/398, 400, 356, 235.8, 237.5, 237.8

[56] References Cited

U.S. PATENT DOCUMENTS 3,658,822 4/1972 Fauran et al. .............. 260/268 BC
4,814,329 3/1989 Harsanyl et al. .............. 514/211

FOREIGN PATENT DOCUMENTS 0074341 3/1983 European Pat. Off. .
0167943 1/1986 European Pat. Off. .
0352864 1/1990 European Pat. Off. .

OTHER PUBLICATIONS

American Journal of Pathology, vol. 139. No. 1, Jul. 1, 1991, pp. 217–229, McGuire et al, "Peroxisome Induction Potential and Lipid–Regulating Activity in Rats".
The Merck Index, 1989, Merck & Co., Rahway USA, p. 1156, No. 7245; 1462–3, No. 9217; and pp. 168–169, Nos. 1091, 1092.
International Journal of Obesity, vol. 11, 1987, pp. 619–629, F. M. Whittington et al, "Effect of Sodium 2–n–pentadecyl–benzimidazole–5–carboxylate . . . and lean mice".

*Primary Examiner*—Raymond J. Henley, III
*Assistant Examiner*—T. J. Criares
*Attorney, Agent, or Firm*—Sughrue, Mion, Zinn, Macpeak & Seas

[57] ABSTRACT

Disclosed are an antihyperlipidemia or antiarteriosclerosis agent comprising a certain benzimidazole or 2,2'-methylenebisphenol derivative such as 5-dodecanoylamino-2-mercaptobenzimidazole or 2,2'-isobutylidenebis(4,6-dimethyphenol).

6 Claims, No Drawings

TREATING ARTERIOSCLEROSIS USING BENZIMIDAZOLE COMPOSITIONS

BACKGROUND OF THE INVENTION

The present invention relates to a novel pharmaceutical composition and method for treating hyperlipidemia and arteriosclerosis, more specifically to an antihyperlipidemia agent having a blood cholesterol lowering effect or an antiarteriosclerosis agent having a macrophage-foaming reaction suppressing effect and a method for treating hyperlipidemia and arteriosclerosis using this composition.

As people have become more affluent, their eating habits have changed toward increased intake of foods with high cholesterol content and high caloric value. As a result, hyperlipidemia and arteriosclerosis are increasing rapidly in conjunction with the aging of the population. This has become a major social problem.

Hitherto, drug therapy for hyperlipidemia and arteriosclerosis has been directed only to lowering blood cholesterol. No drug capable of reversing the effects of arteriosclerosis is available.

Arteriosclerosis is characterized by thickening of the blood vessel intima and lipid deposition within the blood vessel. Therefore, for drug therapy of the disease, drugs capable of lowering blood cholesterol have been used. However, it has been found that the macrophage-foaming reaction plays an important role in forming the focus of arteriosclerosis. Thus, it is expected that suppression of this reaction would result in regression of the arteriosclerosis foci.

SUMMARY OF THE INVENTION

A primary object of the present invention is to provide a novel and low toxic pharmaceutical composition capable of lowering blood cholesterol and suppressing macrophage-foaming reaction by way of inhibiting acyl-CoA cholesterolacyltransferase (ACAT) activity and intracellular cholesterol transport.

Another object of the present invention is to provide a method for treating hyperlipidemia and arteriosclerosis.

These and other objects of the present invention will be apparent from the following description and Examples.

The above objects were achieved based on the discovery that certain benzimidazole and 2,2'-methylenebisphenol derivatives have not only an ACAT activity-inhibiting effect, an intracellular cholesterol transport-inhibiting effect and an excellent blood cholesterol lowering effect but also a macrophage-foaming reaction suppressing effect, and, as such, are able to achieve the aforesaid object.

The first aspect of the present invention relates to a pharmaceutical composition comprising a compound of the following formula (I), (II) or (III), or a pharmaceutically-acceptable salt thereof, or a compound of the following formula (IV) as an active ingredient together with a pharmaceutical-acceptable carrier or diluent:

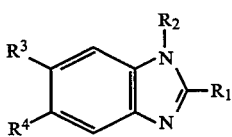

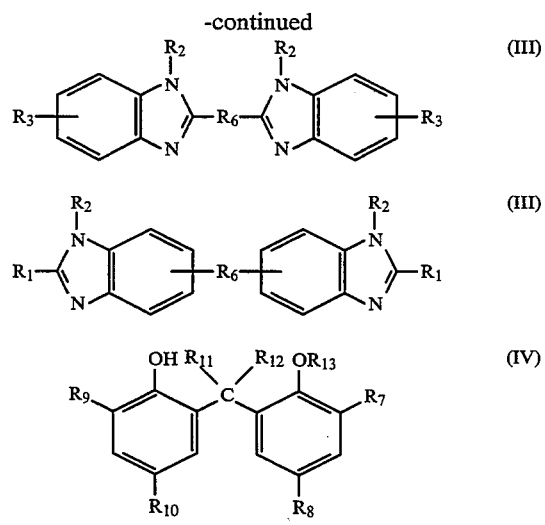

wherein
$R_1$ represents a hydrogen atom, an alkyl, an aryl, a mercapto, an alkylthio, an alkenylthio, an arylthio or a heterocyclo group;

$R_2$ represents a hydrogen atom or an alkyl group, provided that the alkyl group is not substituted by a hydroxyl group;

$R_3$ and $R_4$ each independently represents a hydrogen atom, a halogen atom, a nitro group, $R_5O—$, $R_5CONH—$, $R_5NHCO—$, $(R_5)_2NCO—$, $R_5SO_2NH—$, $R_5NHSO_2—$, $R_5OCO—$, $R_5COO—$ or $R_5NHCONH—$ where $R_5$ represents an alkyl or an aryl group;

$R_6$ represents a divalent group;

$R_7$, $R_8$, $R_9$ and $R_{10}$ each independently represents an alkyl, a cycloalkyl group, $—(C(CH_3)_2)_k—(CH_2)_m COOR_{14}$ or $—(C(CH_3)_2)_k—(CH_2)_m CON(R_{14})_2$ where k represents 0 or 1, m represents an integer of 0 to 4 and $R_{14}$ represents a lower alkyl group;

$R_{11}$ and $R_{12}$ each independently represents a hydrogen atom, an alkyl, an aryl or an aralkyl group; and $R_{13}$ represents a hydrogen atom, a lower alkyl, an aralkyl, an acyl, an alkyl- or arylsulfonyl group, or $—(CH_2)_n COOR_{15}$ where n represents an integer of 0 to 2 and $R_{15}$ represents a lower alkyl group.

The second aspect of the present invention relates to a use of a compound of the formula (I), (II) or (III), or a pharmaceutically-acceptable salt thereof, or a compound of the formula (IV) for preparing an antihyperlipidemia or antiarteriosclerosis agent.

DETAILED EXPLANATION OF PREFERRED EMBODIMENTS

The present invention provides a pharmaceutical composition which has an excellent blood cholesterol lowering effect and macrophagefoaming reaction suppressing effect and is low in toxicity, it therefore exhibits an excellent therapeutic effect on hyperlipidemia and arteriosclerosis and is administrable over a long period.

Among the compounds of the formulae (I), (II), (III) and (IV), the compounds of the formulae (I) and (IV) are preferable and, in the compounds of the formula (I), the compounds of the following formula (V) are particularly preferable;

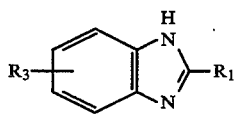

wherein $R_1$ represents a hydrogen atom, an alkyl, a mercapto or an alkylthio group; and $R_3$ represents a hydrogen atom, a halogen atom, a nitro group, $R_5O—$, $R_5CONH—$, $R_5NHCO—$, $R_5NHSO_2—$ or $R_5SO_2NH—$ where $R_5$ represents an alkyl group.

The compounds of the formulae (I), (II), (III) and (V) of the present invention will now be described in detail.

Examples of the alkyl groups represented by $R_1$ in the formulae (I), (III) and (V) include alkyl groups having 1 to 18 carbon atoms (such as methyl, ethyl, butyl, octyl, dodecyl and octadecyl groups). Alkyl groups having 1 to 8 carbon atoms (such as methyl, ethyl, butyl and octyl groups), which may be straight or branched chains, are preferable. Examples of the aryl groups include phenyl and naphthyl groups. Phenyl group is particularly preferable. Examples of the alkyl groups of the alkylthio groups include alkyl groups having 1 to 18 carbon atoms (such as methyl, ethyl, butyl, octyl, dodecyl and octadecyl groups). Alkyl groups having 1 to 8 carbon atoms (such as methyl, ethyl, butyl and octyl groups), which may be straight or branched chains, are preferable. Examples of the alkenyl groups of the alkenylthio groups include alkenyl groups having 2 to 18 carbon atoms (such as allyl and octadecenyl groups). Examples of the aryl groups of the arylthio groups include phenyl and naphthyl groups. Phenyl group is particularly preferable. Examples of the heterocyclo groups of the heterocyclothio groups include pyridyl and hexahydropyridyl groups. 2- and 4-pyridyl groups are particularly preferable.

Each of the alkyl, aryl, alkylthio, alkenylthio, arylthio and heterocyclothio groups represented by $R_1$ may be optionally substituted. Examples of the substituents include halogen atoms, alkyl, aryl, alkoxy, aryloxy, acylamino and nitro groups.

Preferred groups represented by $R_1$ are hydrogen atom, alkyl groups, mercapto group and alkylthio groups. Specific examples of the preferred groups represented by $R_1$ include methyl, butyl, mercapto and methylthio groups.

Next, examples of the alkyl groups represented by $R_2$ in the formulae (I) to (III) include alkyl groups having 1 to 12 carbon atoms (such as methyl, butyl, hexyl, octyl and dodecyl groups). Alkyl groups having 1 to 6 carbon atoms (such as methyl, butyl and hexyl groups), which may be straight or branched chains, are preferable.

The alkyl group represented by $R_2$ may be optionally substituted. Examples of the substituents include aryl, amino and acylamino groups. The alkyl group is not substituted by hydroxy group.

Preferred groups represented by $R_2$ are hydrogen atom and the alkyl groups having 1 to 6 carbon atoms, particularly hydrogen atom.

When $R_3$ in the formulae (I), (II) and (V) and $R_4$ in the formula (I) contain $R_5$, examples of the alkyl groups represented by $R_5$ include alkyl groups having 1 to 20 carbon atoms (such as methyl, butyl, octyl, dodecyl and octadecyl groups). Alkyl groups having 4 to 18 carbon atoms (such as methyl, butyl, octyl, dodecyl and octadecyl groups), which may be straight or branched chains, are preferable. Examples of the aryl groups include phenyl and naphthyl groups. Phenyl group is particularly preferable.

The alkyl and aryl groups represented by $R_5$ may be optionally substituted. Examples of the substituents include halogen atoms, alkyl, aryl, acylamino and aryloxy groups.

Preferred groups represented by $R_3$ and $R_4$ are the above-described groups containing $R_5$, that is, $R_5O—$, $R_5CONH—$, $R_5NHCO—$, $R_5SO_2NH—$, $R_5NHSO_2—$, $R_5OCO—$, $R_5COO—$ and $R_5NHCONH—$, particularly $R_5O—$, $R_5CONH—$, $R_5NHCO—$, $R_5NHSO_2—$ and $R_5SO_2NH—$. Specific examples of the preferred groups include octyloxy, hexadecyloxy, dodecanoyloxy, dodecylcarbamoyl, octylsulfonylamino, dodecylsulfamoyl groups.

Examples of the divalent groups represented by $R_6$ in the formulae (II) and (III) include $—(CH_2)_n—$, $—O(CH_2)_nO—$, $—NHCO(CH_2)_n CONH—$, $—NHSO_2(CH_2)_nSO_2NH—$ where n represents an integer of 1 to 10.

$—(CH_2)_n—$ and $—NHCO(CH_2)_nCONH—$ where n is 2 to 8 are particularly preferable.

Among the above-described compounds having $R_1$ to $R_6$, preferred are the compounds in which at least one substituents have not less than 4 carbon atoms, particularly those in which at least one substituents except for $R_2$ have 4 to 20 carbon atoms, preferably 8 to 18 carbon atoms.

Examples of the parmaceutically-acceptable salts of the compounds represented by the formulae (I), (II) and (III) include hydrochloride, hydrobromide, nitrate, sulfate and toluenesulfonate. Hydrochloride is particularly preferable.

Examples of the compounds of the formulae (I), (II) and (III) or the formula (V) of the present invention are listed below.

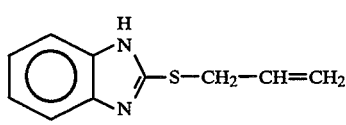

(1)

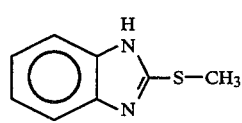

(2)

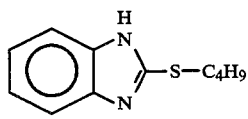

(3)

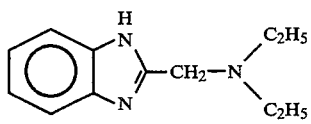

(4)

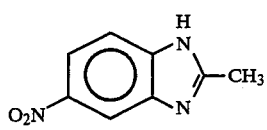 (5)
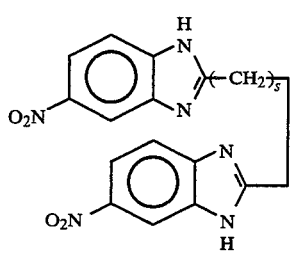 (6)
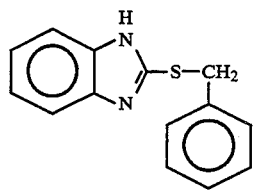 (7)
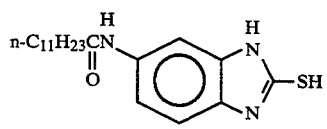 (8)
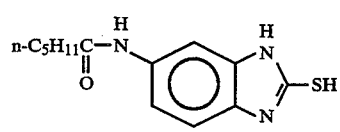 (9)
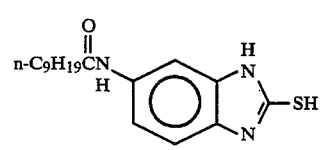 (10)
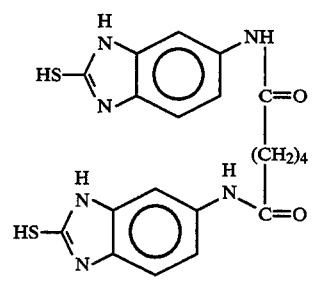 (11)
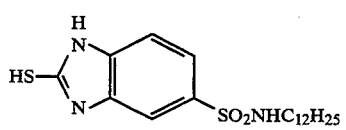 (12)
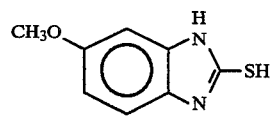 (13)
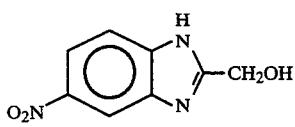 (14)
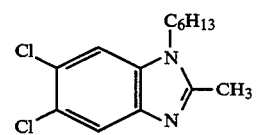 (15)
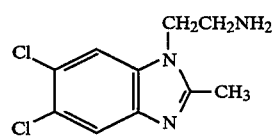 (16)
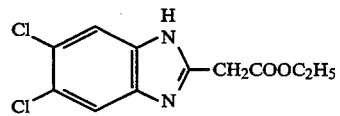 (17)
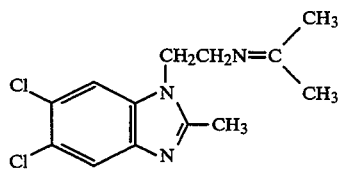 (18)
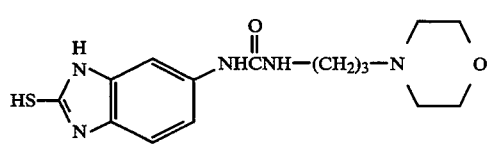 (19)
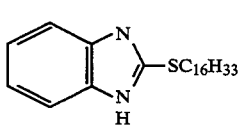 (20)
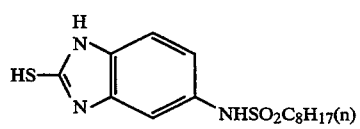 (21)
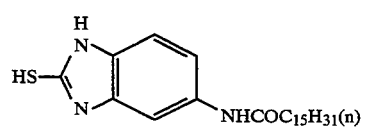 (22)

-continued
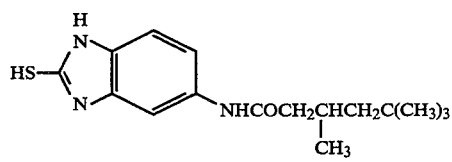 (23)
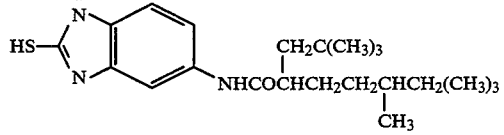 (24)
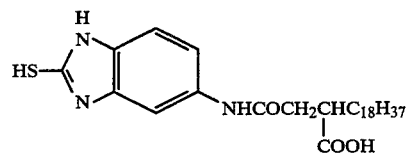 (25)
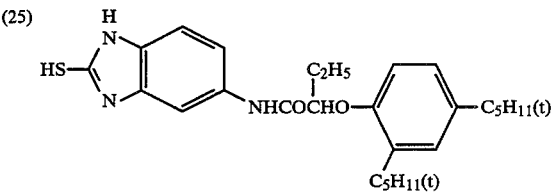 (26)
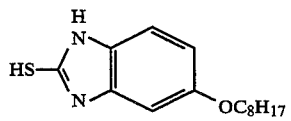 (27)
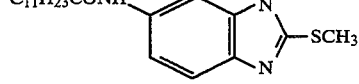 (28)
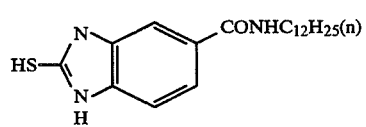 (29)
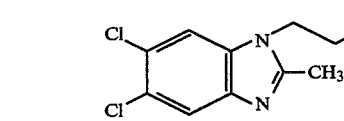 (30)
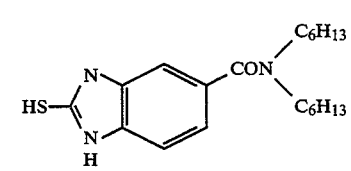 (31)
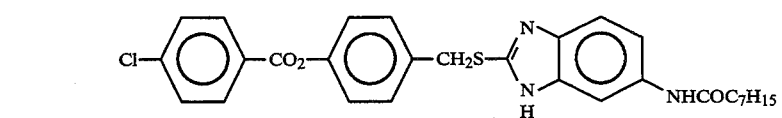 (32)
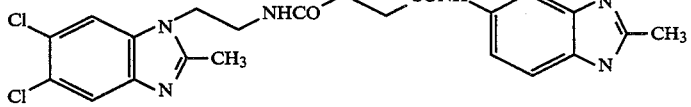 (33)
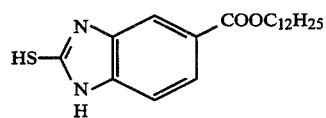 (34)
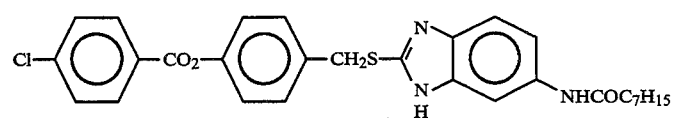 (35)
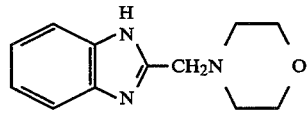 (36)
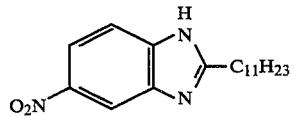 (37)
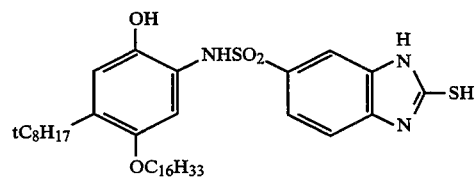 (38)
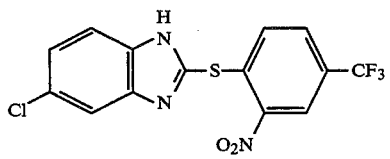 (39)

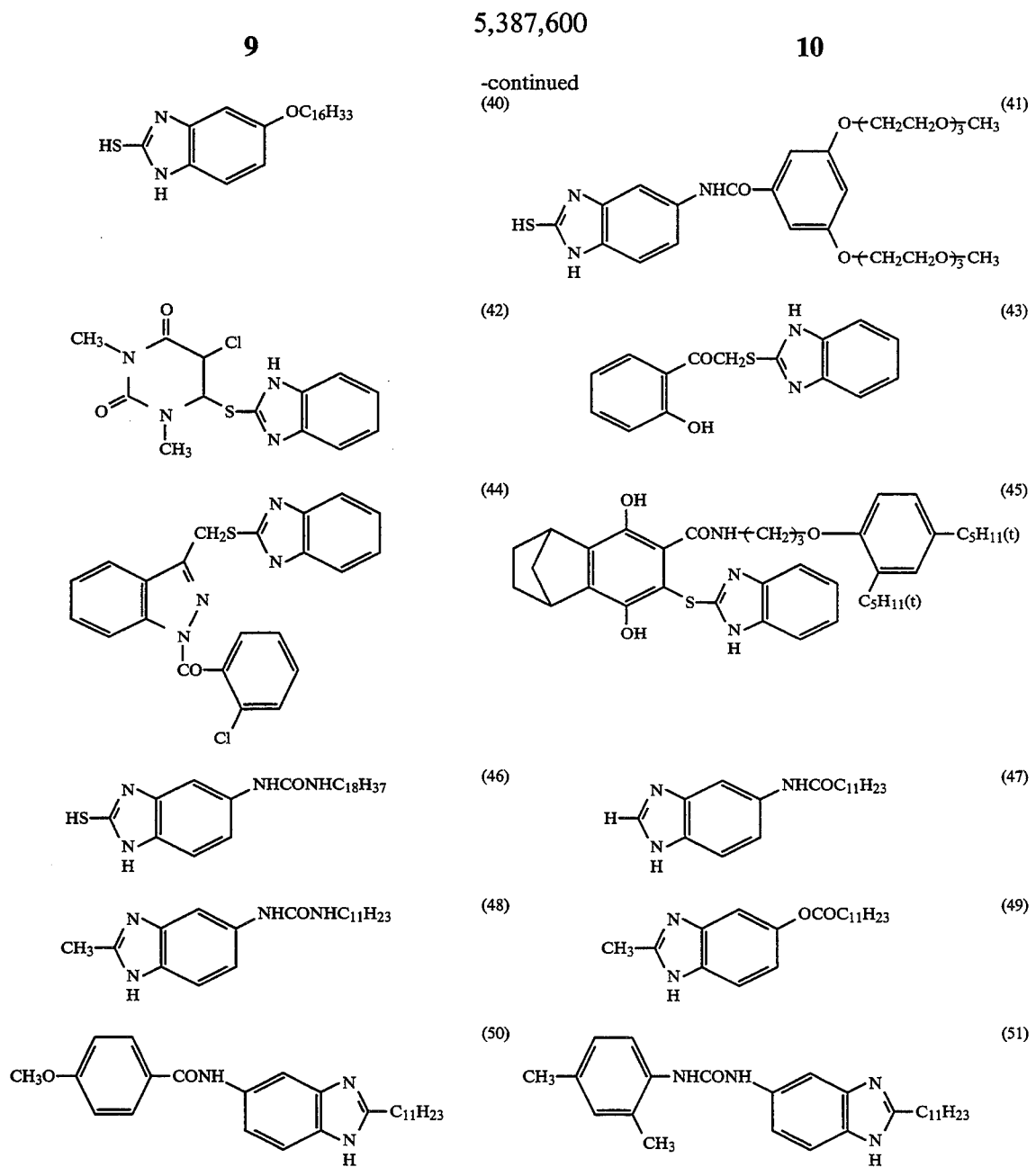

Next, the detailed description will be made on the compounds of the formula (IV) of the present invention.

The alkyl groups represented by $R_7$ to $R_{10}$ in the formula (IV) include alkyl groups having 1 to 12 carbon atoms which may be straight or branched chains. Examples of the alkyl groups include methyl, ethyl, n-propyl, isopropyl, isobutyl, sec-butyl, tert-butyl, tert-pentyl, hexyl, octyl, decyl and dodecyl groups. Among these, alkyl groups having 1 to 8 carbon atoms are preferred and those having 1 to 4 carbon atoms are particularly preferred. However, alkyl groups having not less than 4 carbon atoms are also preferred insofar as they are tertiary alkyl groups (such as tert-butyl, tert-pentyl, tert-hexyl, tert-octyl groups and the like). These alkyl groups may be optionally substituted. Examples of the substituents include halogen atoms such as chlorine, bromine, fluorine and iodine.

The cycloalkyl groups represented by $R_7$ to $R_{10}$ include cyclopentyl, cyclohexyl and cycloheptyl groups. These cycloalkyl groups may be optionally substituted. Examples of the substituents include lower alkyl groups such as methyl and ethyl groups and halogen atoms such as chlorine, bromine, fluorine and iodine. Cycloalkyl groups substituted by methyl group are preferred.

When $R_7$ to $R_{10}$ represent $-(C(CH_3)_2)_k-(CH_2)_m COOR_{14}$ or $-(C(CH_3)_2)_k-(CH_2)_m CON(R_{14})_2$, the lower alkyl groups represented by $R_{14}$ include alkyl groups having 1 to 4 carbon atoms which may be straight or branched chains. Examples of the alkyl groups include methyl, ethyl, n-propyl, isopropyl, isobutyl, sec-butyl and tert-butyl groups, preferably methyl and ethyl groups. k is preferably 1 and m is preferably 3.

Preferable groups represented by $R_7$ to $R_{10}$ are alkyl groups having 1 to 4 carbon atoms and cycloalkyl groups substituted by methyl group, particularly methyl and tert-butyl groups.

The alkyl groups represented by $R_{11}$ and $R_{12}$ in the formula (IV) include alkyl groups having 1 to 13 carbon atoms which may be straight or branched chains. Examples of the alkyl groups include methyl, ethyl, n-propyl, isopropyl, isobutyl, sec-butyl, tert-butyl, hexyl, octyl, decyl and dodecyl groups. Among these, alkyl groups having 1 to 8 carbon atoms are preferred and those having 1 to 4 carbon atoms are particularly preferred.

The aryl groups represented by $R_{11}$ and $R_{12}$ include phenyl, tolyl, xylyl and naphthyl groups. Phenyl group is preferable.

The aralkyl groups represented by $R_{11}$ and $R_{12}$ include benzyl and phenethyl groups.

In the preferable combination of $R_{11}$ and $R_{12}$, one is a hydrogen atom and the other is a lower alkyl group having 1 to 4 carbon atoms.

The lower alkyl groups represented by $R_{13}$ in the formula (IV) include alkyl groups having 1 to 4 carbon atoms which may be straight or branched chains. Examples of the alkyl groups include methyl, ethyl, n-propyl, isopropyl, isobutyl, sec-butyl and tert-butyl groups. Methyl and ethyl groups are preferable.

The aralkyl groups represented by $R_{13}$ include benzyl and phenethyl groups.

The acyl groups represented by $R_{13}$ include aliphatic and aromatic acyl groups. Examples of the aliphatic acyl groups include acyl groups having 2 to 6 carbon atoms (such as acetyl, propionyl, pentanoyl and the like), which may be straight or branched chains. Examples of the aromatic acyl groups include benzoyl group. These acyl groups may be optionally substituted. Examples of the substituents of the aliphatic acyl groups include lower alkoxy groups and phenoxy group. These substituents may further be substituted by one or more substituents including lower alkyl groups such as methyl, ethyl, n-propyl, isopropyl, isobutyl, sec-butyl and tert-butyl groups and halogen atoms such as chlorine, bromine, fluorine and iodine. Examples of the substituents of the aromatic acyl groups include lower alkyl groups such as methyl, ethyl, n-propyl, isopropyl, isobutyl, sec-butyl and tert-butyl groups and halogen atoms such as chlorine, bromine, fluorine and iodine.

Examples of the alkylsulfonyl groups represented by $R_{13}$ include alkylsulfonyl groups having 2 to 4 carbon atoms (such as methanesulfonyl, ethanesulfonyl, propanesulfonyl and the like), which may be straight or branched chains. Examples of the arylsulfonyl groups represented by $R_{13}$ include benzenesulfonyl and p-toluenesulfonyl groups.

When $R_{13}$ represents $-(CH_2)_nCOOR_{15}$, the lower alkyl groups represented by $R_{15}$ include alkyl groups having 1 to 4 carbon atoms which may be straight or branched chains. Examples of the alkyl groups include methyl, ethyl, n-propyl, isopropyl, isobutyl, sec-butyl and tert-butyl groups. Methyl and ethyl groups are preferable. n is preferably 0 or 1.

$R_{13}$ is preferably a hydrogen atom.

Examples of the compounds of the general formula (IV) of the present invention are listed below.

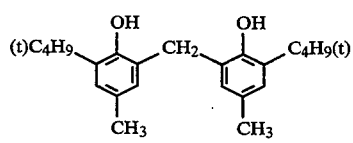

(52)

-continued

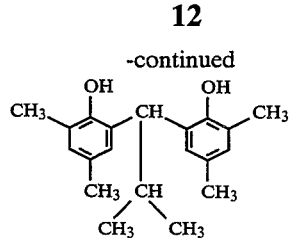

(53)

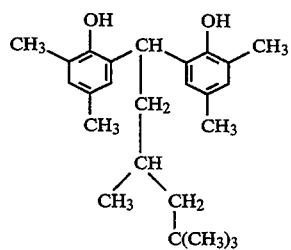

(54)

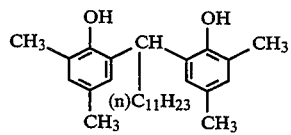

(55)

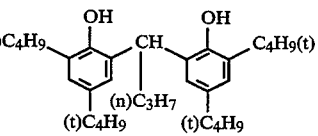

(56)

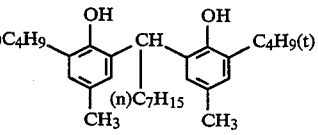

(57)

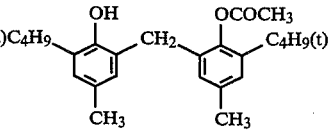

(58)

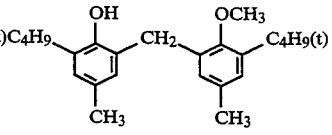

(59)

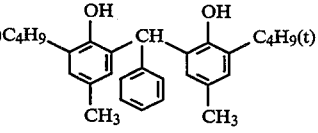

(60)

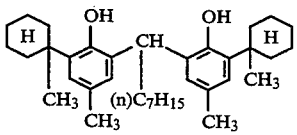

(61)

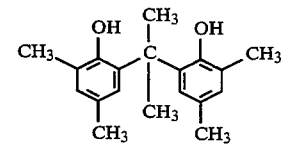

(62)

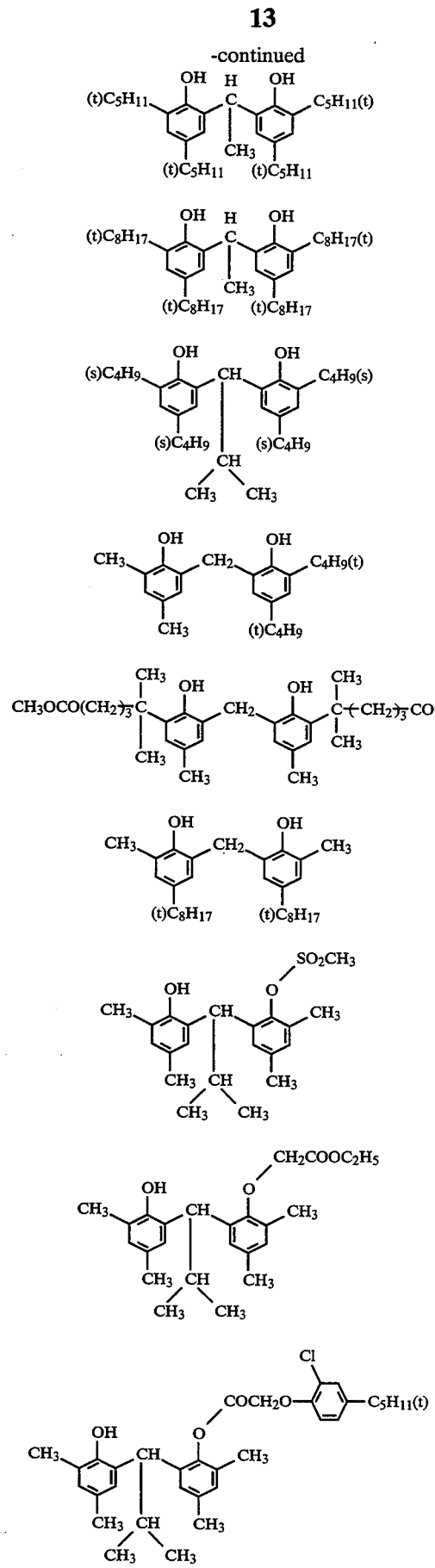
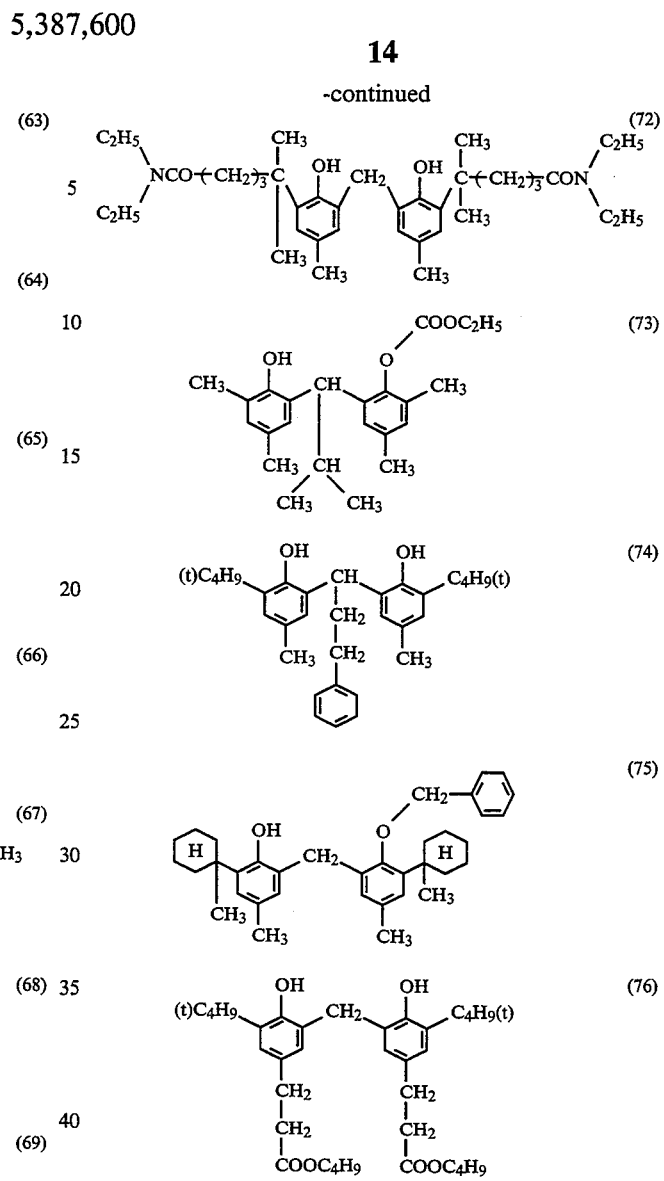

The method for preparing these compounds will now be described in detail.

Benzimidazole ring which is basic skeleton of the compounds of the formulae (I), (II) and (III) is generally synthesized using a o-phenylenediamine as a starting material. That is 2-mercaptobenzimidazoles are generally synthesized by reacting o-phenylenediamines with carbon disulfide under a basic condition and 2-alkyl- or 2-aryl benzimidazoles are generally synthesized by reacting o-phenylenediamines with carboxylate or orthocarboxylate under an acidic condition.

On the other hand, 2,2'-methylenebisphenol derivatives of the compounds of the formula (IV) are generally synthesized by subjecting a phenol and an aldehyde or ketone to dehydrocondensation under an acidic condition. However, it is possible to obtain the compounds by subjecting a phenol derivative and an aldehyde or ketone to equimolar addition reaction under a basic condition to obtain a methylol intermediate and then reacting this intermediate with the equimolar phenol under an acidic condition. The latter method is particularly useful for preparing an unsymmetrical 2,2'-methylenebisphenol derivative.

Synthesis Example 1

Synthesis of 2-metyl-5-nitrobenzimidazole (5)

15.3 g of 3,4-dinitrobenzene was added to 64 ml of acetic anhydride and 2 ml of conc. hydrochloric acid and the mixture was refluxed for 3 hours. After cooling, the formed crystals were dispersed in 10% sodium hydroxide aqueous solution and then filtered off. The crystals were recrystallized from water-containing ethanol to obtain 6 g of compound (5).

Melting point: 220°–221° C. Elemental analysis (%): Anal. C 54.42 H 4.03 N 23.62 Cal. C 54.23 H 3.98 N 23.72

Synthesis Example 2

Synthesis of 1,8-bis(5-nitrobenzimidazol-2-yl) octane (6)

10.8 g of o-phenylenediamine and 10.1 g of sebacic acid were added to 120 ml of 4N hydrochloric acid and the mixture was refluxed for 6 hours. After cooling, the formed crystals were filtered off and washed with 1N sodium carbonate aqueous solution until the washing solution maitained an alkalinity. After separating and drying the crystals, they were dissolved in 35 ml of conc. sulfuric acid and 3.8 g of potassium nitrate was added thereto little by little while stirring under cooling with ice. After stirring for 2 hours under cooling with ice, the solution was poured into ice-water and the formed crystals were washed with 1N sodium carbonate aqueous solution until the washing solution maitained an alkalinity. The crystals were recrystallized from water-containing ethanol to obtain 3.4 g of compound (6).

Melting point: 135°–137° C. Elemental analysis ( % ): Anal. C 60.62 H 19.25 N 5.41 Cal. C 60.54 H 19.26 N 5.54

Synthesis Example 3

Synthesis of 2-mercapto-5-methoxybenzimidazole (13)

70 ml of ethanol and 15 ml of carbon disulfide were added to 2.6 g of 3,4-diaminoanisole and then a solution of 1.5 g of sodium hydroxide in 5 ml of water was added thereto. After heating with a water bath for 3.5 hours, the mixture was cooled with ice, filtered and then the solvent in the filtrate was distilled off under reduced pressure. The residue was dissolved in ethanol. The solution was filtrated to remove the insoluble matter and then the solvent in the filtrate was distilled off under reduced pressure. The residue was recrystallized from water-containing methanol to obtain 2.0 g of the titled compound (13).

Melting point: 254°–255° C. Elemental analysis (%): Anal. C 53.06 H 4.52 N 15.27 Cal. C 53.33 H 4.44 N 15.56

Synthesis Example 4

Synthesis of 2-benzylthiobenzimidazole (7)

15 g of 2-mercaptobenzimidazole and 16.5 g of benzylbromide were dissolved in 50 ml of ethanol and the mixture was refluxed with a water bath for 5 hours. After cooling, the formed crystals were collected and recrystallized from ethanol to obtain 18 g of compound (7).

Melting point: 185°–186° C. Elemental analysis (%): Anal. C 69.59 H 5.30 N 11.74 Cal. C 69.99 H 5.03 N 11.66

Synthesis Example 5

Synthesis of 5-dodecanoylamino-2-mercaptobenzimidazole (8)

5 g of 5-amino-2-mercaptobenzimidazole was dissolved in 50 ml of pyridine and 7.95 g of dodecanoyl chloride was added dropwise thereto under cooling with ice. After stirring, for 3 hours at room temperature, the solution was poured into ice-water. The formed crystals were filtered off and recrystallized from water-containing methanol to obtain 10.9 g of compound (8).

Melting point: 266°–267° C. Elemental analysis (%): Anal. C 66.38 H 8.54 N 11.34 Cal. C 65.71 H 8.36 N 12.10

Synthesis Example 6

Synthesis of 2-morpholinomethylbenzimidazole (36)

To 108 g of o-phenylenediamine, 1 l of 4N hydrochloric acid and 142 g of chloroacetic acid were added and refluxed for 1.5 hours. After allowing to stand overnight, the solution was diluted with 2 l of water and neutralized with dilute ammonia water. The formed crystals were filtered off to obtain 113 g of 2-chloromethylbenzimidazole.

10 g of 2-chloromethylbenzimidazole thus obtained and 10.5 g of morpholine were dissolved in 75 ml of alcohol and the solution was refluxed for 3 hours. After cooling, ether was added to the solution and the precipitated crystals were filtered off. The filtrate was washed with water and satuluted with hydrogen chloride to form an oily matter. The oily matter was crystallized by adding a smoll amount of alcohol and the crystals were, filtered off. The crystals were recrystallized from alcohol to obtain 2.5 g of compound (36).

Melting point: 235°–236° C. Elemental analysis (%): Anal. C 49.48 H 5.88 N 14.27 Cal. C 49.66 H 5.91 N 14.48

Synthesis Example 7

Synthesis of 2,2'-isobutylidenebis(4,6-dimethyphenol) (53)

36 g of isobutylaldehyde and 122 g of 2,4-dimethyphenol were mixed and 77 g of anhydrous calcium chloride was added to this mixture. The resulting mixture was heated to 60° C. and 46 ml of conc. hydrochloric acid was added dropwise over 2 hours. After stirring for 6 hours, the reaction mixture was cooled and then water and methanol were added to disperse solid matter. After filtration, the solid matter was washed with water, dried and recrystallized from hexane under cooling to obtain 102 g of compound (53).

Melting point: 163°–165° C. Elemental analysis (%): Anal. C 80.67 H 8.88 Cal. C 80.49 H 8.78

Synthesis Example 8

Synthesis of 2,2'-methylenebis (6-tert-butyl-4-methylphenol) monomethyl ether (59)

34 g of 2,2'-methylenebis(6-tert-butyl-4-methylphenol) was dissolved in 50 ml of acetone and 27.6 g of anhydrous calcium chloride was added to this solution. 15 g of methyl iodide was slowly added dropwise thereto while stirring under reflux. After stirring for 6 hours, the reaction mixture was cooled and solid matter was filtered off. The filtrate was poured into ice-water and the formed crystals were filtered off. The crystals were recrystallized from water-containing methanol to obtain 28.2 g of compound (59).

Melting point: 163°–165° C. Elemental analysis (%): Anal. C 81.06 H 9.54 Cal. C 81.31 H 9.67

Synthesis Example 9

Synthesis of 2,2'-ethylidenebis(4,6-di-tert-pentylphenol) (63)

70.4 g of 2,4-di-tert-pentylphenol and 9.9 g of paraformaldehyde were dissolved in 100 ml of toluene and 5.7 g of p-toluenesulfonic acid was added thereto. The solution was heated to 70° C. and 30 ml of toluene was distilled off over 3 hours under reduced pressure of 100–135 mmHg. After cooling, water was added to the solution and the water phase was neutralized with sodium hydrogen carbonate. Then, the toluene phase was washed with water, the solvent was distilled off under reduced pressure and the residue was recrystallized from water-containing methanol to obtain 52 g of compound (63).

Melting point: 116°–118° C. Elemental analysis (%): Anal. C 82.67 H 10.92 Cal. C 82.53 H 11.00

The following compounds were synthesized according to the method above described. The melting points of the crystalline compounds are as follows:

| Compound No. | m.p.(°C.) | Compound No. | m.p.(°C.) |
| --- | --- | --- | --- |
| (1) | 195–200 (HCl salt) | (2) | 200–203 |
| (3) | 133–135 (HBr salt) | (4) | 167–170 |
| (5) | 220–221 | (6) | 135–137 |
| (7) | 190–191 | (8) | 226–267 |
| (9) | 266–268 | (10) | 275–276 |
| (11) | >300 | (12) | >280 |
| (13) | 254–255 | (14) | 128–129 |
| (15) | 95–97 | (16) | 106–108 |
| (17) | 181–183 | (18) | 119–123 |
| (20) | 84–87 | (21) | 183–186 |
| (23) | 250–252 | (24) | 214–217 |
| (25) | 200 (decomp.) | (26) | 284–286 |
| (27) | 230–232 | (28) | 132–134 |
| (29) | 217 (decomp.) | (30) | 243–245 |
| (31) | 143–144 | (32) | >250 |
| (33) | 124–125 | (34) | 218–220 |
| (35) | 215–217 (HCl salt) | (36) | 235 (decomp.) (HCl salt) |
| (37) | 162–164 | (38) | 215–216 |
| (39) | 202–203 | (42) | 230–231 |
| (43) | 155–156 | (44) | 163–164 |
| (45) | 146 (decomp.) | (46) | 197–199 |
| (47) | 54–56 | (48) | 60–63 |
| (49) | 82–85 | (50) | 188–191 |
| (51) | 209–212 | | |
| (52) | 123–124 | (53) | 163–165 |
| (54) | 171–173 | (55) | 124–125 |
| (56) | 117–118 | (57) | 105–106 |
| (58) | 98–101 | (59) | 120–123 |
| (60) | 171–172 | (61) | 92–95 |
| (62) | 128–131 | (63) | 116–118 |
| (64) | 101–102 | (67) | 53–56 |
| (68) | 162–165 | (74) | 139–140 |

Compounds (65), (72) and (73) are oily and compounds (66), (69), (70), (71), (75) and (76) are non-crystalline. Accordingly, they have no melting point.

The pharmaceutical composition of the present invention may contain one or more compounds of formulae (I) to (IV) and may be used in combination with the known antihyperlipidemia and antiarteriosclerosis agents that are conventionally used and are compatible with the compounds of the present invention. Examples of known antihyperlipidemia and antiarteriosclerosis agents include Melinamide, Probucol and Mevalotin.

The pharmaceutical composition of the present invention may be administered, for example, orally or by injection (mainly intramuscular, intravenous or subcutaneous route) and is usually prepared in the form of a formulation suitable for the administration route. Thus, the pharmaceutical composition can be used as an oral formulation such as tablet, powder, granule, capsule, syrup, emulsion, suspension or solution, or injection. The formulations can be prepared by mixing the compound of the present invention with a pahrmaceutical-acceptable carrier, diluent and/or bioactive substance.

Examples of pharmaceutical carriers or diluents suitable for combining with the compound of formula (I) to (IV) include glucose; saccharose; lactose; ethanol; glycerin; mannitol; sorbitol; pentaerythritol; diethylene glycol, triethylene glycol, ethylene glycol, propylene glycol, dipropylene glycol, polyethylene glycol 400, other polyethylene glycols than polyethylene glycol 400; mono-, di- and triglycerides of saturated fatty acids such as trilauryl glyceride, monostearoyl glyceride, tristearoyl glyceride and distearoyl glyceride; pectin; starch; corn starch; arginic acid; xylose; talc, lycopodium; oils and fats such as olive oil, peanut oil, castor oil, corn oil, wheat malt oil, sesame oil, cottonseed oil, sunflower oil and cod-liver oil; gelatin; lecithin; silica; cellulose; cellulose derivatives such as hydroxypropyl methyl cellulose, methylcellulose, hydroxyethyl cellulose and calcium carboxymethyl cellulose; magnesium or calcium salts of fatty acids having 12 to 22 carbon atoms such as calcium stearate, calcium laurate, magnesium oleate, calcium palmitate, calcium behenate and magnesium stearate; cyclodextrins such as α-cyclodextrin, β-cyclodextrin, τ-cyclodextrin, hydroxyethyl-β-cyclodextrin, hydroxypropyl-β-cyclodextrin, dihydroxypropyl-β-cyclodextrin, carboxymethyl ethyl-β-cyclodextrin and dimethyl-β-cyclodextrin; emulsifiers such as esters of saturated and unsaturated fatty acids having 2 to 22, particularly 10 to 18 carbon atoms, with monovalent aliphatic alcohols (for example, alkanols having 1 to 20 carbon atoms such as glycol, glycerin, diethylene glycol, pentaerythritol, ethanol, butanol and octadecanol) or polyvalent alcohols; silicones such as dimethyl polysiloxane; and pyrogen-free distilled water.

The dosage of the pharmaceutical composition of the present invention varies depending on age, body weight, severity of the disease of the patient and the administration route. However, in general, the quantity of the compound of formula (I), (II), (III) and/or (IV) to be administered ranges from 0.1 to 500 mg, preferably from 0.2 to 100 mg per day per kg of body weight for adult.

Pharmaceutical Test (1) In vitro test for suppressing effect of macrophage-foaming reaction using mouse abdominal cavity macrophage A 15-week old ICR female mouse (Japan SLC) was amputated at its neck and exsanguinated. Then, Hanks buffer (Nissui Pharmaceutical Co., Ltd.) was injected intraperitoneally. After massaging the abdominal part, the buffer was recovered rapidly and centrifuged at 1,000 rpm for 5 minutes to collect the abdominal cavity macrophage. Then, the collected abdominal cavity macrophage was suspended in GIT medium (Wako Pure Chemical Industry) and inoculated on a 24-well microplate. After culturing the macrophage for 2 hours at 37° C. in 5% $CO_2$, the medium was changed into Dulbecco modified Eagle's MEM medium (Nissui Pharmaceutical Co., Ltd.). After further culturing the macrophage for 16 hours at 37° C. in 5% $CO_2$, the following substances were added in order:

① Test compounds: solutions in DMSO (Wako Pure Chemical Industry) 1 ml of the solutions were prepared, optionally diluted and the diluted solutions were added to individual wells (500 μl) in the amount of 5μl.

② Liposome
PC/PS/DCP/CHOL.=50/50/10/75 (nmol)
PC: phosphatidylcholine (Funakoshi)
PS: phosphatidylserine (Funakoshi)
DCP: dicetylphosphate (Funakoshi)
CHOL.: cholesterol (Sigma)

③ $^3$H-Oleic acid (Amersham Japan)

Then, after still further culturing the macrophage for 16 hours at 37° C. in 5% $CO_2$, the lipid fraction was extracted with chloroform and methanol. The extracted lipid fraction was subjected to TLC (hexane:ether:acetic acid=70:30:1), the separated bands of CE (cholesteryl ester) and TG (triglyceride) were borne off from the TLC plate and then the radioactivities thereof were measured using a liquid scintillation counter (PACKARD BH-22). Yields of cholesteryl ester were calculated by comparing with a control. The results are shown in Table 1.

TABLE 1

| Compound No. | Dosage | Yield of CE (%) | Yield of TG (%) |
|---|---|---|---|
| (3) | 5 μM | 69 | 89 |
| (5) | 5 μM | 67 | 89 |
| (6) | 5 μM | 8.0 | 61 |
| (7) | 5 μM | 61 | 91 |
| (8) | 5 μM | 42 | 106 |
| (10) | 5 μM | 69 | 129 |
| (12) | 5 μM | 52 | 102 |
| (20) | 5 μM | 49 | 62 |
| (21) | 5 μM | 64 | 93 |
| (23) | 5 μM | 56 | 119 |
| (27) | 5 μM | 51 | 78 |
| (28) | 5 μM | 53 | 164 |
| (30) | 5 μM | 51 | 91 |
| (34) | 5 μM | 50 | 108 |
| (42) | 5 μM | 61 | 96 |
| (43) | 5 μM | 45 | 98 |
| (47) | 5 μM | 55 | 98 |
| (52) | 5 μM | 38 | 101 |
| (53) | 5 μM | 56 | 92 |
| (54) | 5 μM | 25 | 95 |
| (56) | 5 μM | 51 | 102 |
| (58) | 5 μM | 45 | 98 |
| (60) | 5 μM | 48 | 96 |
| (61) | 5 μM | 52 | 103 |
| (62) | 5 μM | 61 | 98 |
| (63) | 5 μM | 42 | 96 |
| (65) | 5 μM | 38 | 101 |
| (66) | 5 μM | 54 | 108 |
| (67) | 5 μM | 42 | 92 |
| (68) | 5 μM | 53 | 86 |
| (73) | 5 μM | 48 | 90 |
| (74) | 5 μM | 65 | 108 |

It is clear from Table 1 that these compounds do not lower the yield of TG so far, that is, these compounds are low toxic and capable of markedly suppressing the yield of CE. Namely, these compounds markedly suppress the macrophage-foaming reaction without being highly toxic to the macrophage.

(2) Blood lipid lowering effect in rabbit fed high-cholesterol feed (i) New Zealand White female rabbits having body weight of about 2 kg were fed feed having high cholesterol content (100 g/day/rabbit: ORC-4 manufactured by Oriental Yeast, containing 0.5% of cholesterol and 0.5% of olive oil) for 7 days to produce hypercholesterolemia.

Subsequently, one group consisting of 3 rabbits (treatment group) was fed the same feed in the same amount, except that the feed further contained test compound (8) in the amount of 100 mg/kg/day/rabbit, for 7 successive days. On the other hand, as a control, another group consisting of 3 rabbits was fed the same feed in the same amount without any test compound.

A small amount of blood was drawn from the parotic vein of every rabbit once a week and was measured for amount of blood total cholesterol using IATROLIPO TC manufactured by Iatron Laboratories Inc.

The amount of blood total cholesterol of the treatment group fell by 25% in comparison with the control group (3 rabbits).

Thus, it is clear that test compound (8) has an excellent lowering effect of the blood cholesterol. (ii) New Zealand White female rabbits having body weight of about 2 kg were fed feed having high cholesterol content (100 g/day/rabbit: ORC-4 manufactured by Oriental Yeast, containing 0.5% of cholesterol and 0.5% of olive oil) for 7 days to produce hypercholesterolemia.

Subsequently, one group consisting of 3 rabbits (treatment group) was fed the same feed in the same amount, except that the feed further contained test compound (53) in the amount of 100 mg/kg/day/rabbit, for 7 successive days. On the other hand, as a control, another group consisting of 3 rabbits was fed the same feed in the same amount without any test compound.

A small amount of blood was drawn from the parotic vein of every rabbit once a week and was measured for amount of blood total cholesterol using IATROLIPO TC manufactured by Iatron Laboratories Inc.

The amount of blood total cholesterol of the treatment group fell by 40% in comparison with the control group (3 rabbits).

In the same manner, Probucol, a conventional drug, was successively administered in the amount of 100 mg/kg/day for 7 days. In this case, the amount of blood total cholesterol of the treatment group fell by 15 to 20% in comparison with the control group.

Thus, it is clear that test compound (53) has an excellent blood cholesterol lowering effect in comparison with the conventional drug.

(3) Blood lipid lowering effect in rabbit fed normal feed (i) New Zealand White female rabbits having body weight of about 2 kg were fed normal feed (100 g/day/rabbit: ORC-4 manufactured by Oriental Yeast) for 7 days.

Subsequently, one group consisting of 3 rabbits (treatment group) was fed the normal feed in the same amount, except that the feed further contained test compound (8) in the amount of 100 mg/kg/day/rabbit, for 7 successive days. As a control, another group consisting of 3 rabbits was fed the normal feed in the same amount without any test compound.

A Small amount of blood was drawn from the parotic vein of every rabbit once a week and was measured for amount of blood total cholesterol using IATROLIPO TC manufactured by Iatron Laboratories Inc.

The amount of blood total cholesterol of the treatment group fell by 20% in comparison with the control group (3 rabbits).

Thus, it is clear that test compound (8) has an excellent blood cholesterol lowering effect not only on rabbits fed high-cholesterol feed but also on rabbits fed normal feed. (ii) New Zealand White female rabbits having body weight of about 2 kg were fed normal feed (100 g/day/rabbit: ORC-4 manufactured by Oriental Yeast) for 7 days.

Subsequently, one group consisting of 3 rabbits (treatment group) was fed with the normal feed in the same amount, except that the feed further contained test compound (53) in the amount of 100 mg/kg/day/rabbit, for 7 successive days. As a control, another group consisting of 3 rabbits was fed the normal feed in the same amount without any test compound.

A small amount of blood was drawn from the parotic vein of every rabbit once a week and was measured for amount of blood total cholesterol using IATROLIPO TC manufactured by Iatron Laboratories Inc.

The amount of blood total cholesterol of the treatment group fell by 20% in comparison with the control group (3 rabbits).

Thus, it is clear that test compound (53) has an excellent blood cholesterol lowering effect not only on rabbits fed high-cholesterol feed but also on rabbits fed normal feed.

(4) Arteriosclerosis focus formation-regressing effect in rabbit fed feed having high cholesterol content New Zealand White female rabbits having body weight of about 2 kg were fed feed having high cholesterol content (100 g/day/rabbit: ORC-4 manufactured by Oriental Yeast, containing 0.5% of cholesterol and 0.5% of olive oil) for 7 days to produce hypercholesterolemia.

Subsequently, one group consisting of 3 rabbits (treatment group) was fed the same feed in the same amount, except that the feed further contained test compound (53) in the amount of 100 mg/kg/day/rabbit, for 20 successive days. On the other hand, as a control, another group consisting of 3 rabbits was fed the same feed in the same amount without any test compound.

After 20 weeks from the administration of the test compound, the aortas and arch part thereof were removed from each rabbit and the blood vessels were opened. Comparing the treatment group with the control group, it was observed that the arteriosclerosis focus formation was suppressed effectively in the treatment group. It was also observed that the test compound suppressed the cholesterol deposition to the eye ball and fatty liver formation.

Namely, test compound (53) not only lowers the blood cholesterol value but also suppresses arteriosclerosis focus formation. In addition, test compound (53) has effect of suppressing fatty liver formation and cholesterol deposition to the eye ball.

(5) Acute toxicity test

Compounds (8) and (53) each was suspended in 0.5% Tween 80 solution. Six 8-week old ddy mice were orally administered the suspensions respectively and were observed on acute toxicity. As a result, the LD50 value of the compounds of the present invention were found to be not less than 1000 mg/kg. This value indicates that the compounds of the present invention is low in toxicity.

EXAMPLES

Example 1

Tablet

Preparation of tablet containing 25 mg of compound (8)

| | | |
|---|---|---|
| ① compound (8) | 10 g | |
| ② corn starch | 40 g | |
| ③ crystalline cellulose | 45 g | |
| ④ calcium carboxylmethyl cellulose | 4 g | |
| ⑤ light silicic acid anhydride | 500 mg | |
| ⑥ magnesium stearate | 500 mg | |
| Total | 100 g | |

① to ⑥ were homogeneously mixed and the resulting mixture was compression molded with a tableting machine to obtain tablets having weight of 250 mg. Each of these tablets contained 25 mg of compound (8). An adult may take 5 to 30 tablets over the course of one day.

Example 2

Tablet

Preparation of tablet containing 25 mg of compound (53)

| | |
|---|---|
| ① compound (53) | 10 g |
| ② corn starch | 40 g |
| ③ crystalline cellulose | 45 g |
| ④ calcium carboxylmethyl cellulose | 4 g |
| ⑤ light silicic acid anhydride | 500 mg |
| ⑥ magnesium stearate | 500 mg |
| Total | 100 g |

① to ⑥ were homogeneously mixed and the resulting mixture was compression molded with a tableting machine to obtain tablets having weight of 250 mg. Each of these tablets contained 25 mg of compound (53). An adult may take 5 to 30 tablets over the course of one day.

Example 3

Capsule

Preparation of capsule containing 40 mg of compound (8)

| | |
|---|---|
| ① compound (8) | 20 g |
| ② corn starch | 79.5 g |
| ③ light silicic acid anhydride | 500 mg |
| Total | 100 g |

① to ③ were homogeneously mixed and the resulting mixture was encapsulated in the amount of 200 mg per capsule. Each of thus-obtained capsules contained 40 mg of compound (8). An adult may take 1 to 20 capsules over the course of one day.

Example 4

Capsule

Preparation of capsule containing 40 mg of compound (53)

| | |
|---|---|
| ① compound (53) | 20 g |
| ② corn starch | 79.5 g |
| ③ light silicic acid anhydride | 500 mg |
| Total | 100 g |

① to ③ were homogeneously mixed and the resulting mixture was encapsulated in the amount of 200 mg per capsule. Each of thus-obtained capsules contained 40 mg of compound (53). An adult may take 1 to 20 capsules over the course of one day.

Example 5

Granule

Preparation of granule containing 100 mg of compound (8) per 1 g

| | |
|---|---|
| ① compound (8) | 10 g |
| ② corn starch | 40 g |
| ③ 10% hydroxypropyl cellulose solution in ethanol | 50 g |
| Total | 100 g |

① to ⑥ were homogeneously mixed. After kneading, the mixture was granulated with a granulating machine and dried to obtain granules. These capsules contained 100 mg of compound (8) per 1 g. An adult may take 1 to 8 g over the course of one day.

Example 6

Granule

Preparation of granule containing 100 mg of compound (53) per 1 g

| | |
|---|---|
| ① compound (53) | 10 g |
| ② crystalline cellulose | 40 g |
| ③ 10% hydroxypropyl cellulose solution in ethanol | 50 g |
| Total | 100 g |

① to ③ were homogeneously mixed. After kneading, the mixture was granulated with a granulating machine and dried to obtain granules. These capsules contained 100 mg of compound (53) per 1 g. An adult may take 1 to 8 g over the course of one day.

We claim:

1. A method for treating arteriosclerosis which comprises administering an effective amount of the pharmaceutical composition to a mammal suffering from arteriosclerosis, wherein the pharmaceutical composition comprises a compound of the following formula (I), (II) or (III), or a pharmaceutically-acceptable salt thereof, as an active ingredient together with a pharmaceutically-acceptable carrier or diluent:

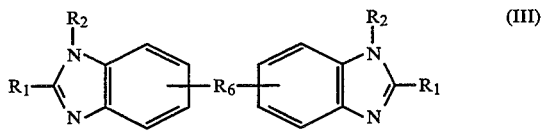

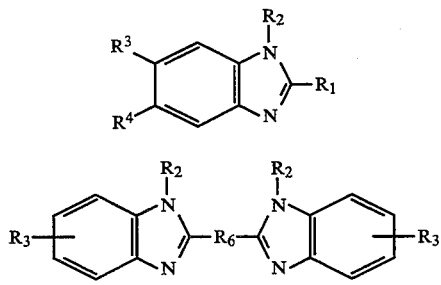

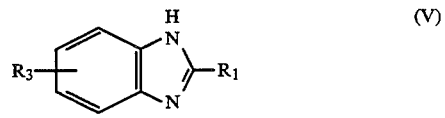

wherein $R_1$ represents a hydrogen atom, an alkyl, an aryl, a mercapto, an alkylthio, an alkenylthio, an arylthio or a heterocyclo group;

$R_2$ represents a hydrogen atom or an alkyl group, provided that the alkyl group is not substituted by a hydroxyl group;

$R_3$ and $R_4$ each independently represents a hydrogen atom, a halogen atom, a nitro group, $R_5O-$, $R_5CONH-$, $R_5NHCO-$, $(R_5)_2NCO-$, $R_5SO_2NH-$, $R_5NHSO_2-$, $R_5OCO-$, $R_5COO-$ or $R_5NHCONH-$ where $R_5$ represents an alkyl or an aryl group; and $R_6$ represents a divalent group.

2. The method according to claim 1, wherein the mammal is a human.

3. The method according to claim 1, wherein the active ingredient in the pharmaceutical composition is the compound of the formula (I).

4. The method according to claim 3, wherein the compound of the formula (I) is represented by the following formula (V);

(V)

wherein $R_1$ represents a hydrogen atom, an alkyl, a mercapto or an alkylthio group; and $R_3$ represents a hydrogen atom, a halogen atom, a nitro group, $R_5O-$, $R_5CONH-$, $R_5NHCO-$, $R_5NHSO_2-$ or $R_5SO_2NH-$ where $R_5$ represents an alkyl group.

5. The method according to claim 4, wherein $R_1$ represents a hydrogen atom, an alkyl group having 1 to 18 carbon atoms, a mercapto group or an alkylthio group having 1 to 18 carbon atoms; and $R_5$ represents an alkyl group having 1 to 20 carbon atoms.

6. The method according to claim 4, wherein $R_1$ represents a hydrogen atom, an alkyl group having 1 to 8 carbon atoms, a mercapto group or an alkylthio group having 1 to 8 carbon atoms; and $R_5$ represents an alkyl group having 4 to 18 carbon atoms.

* * * * *